US012734282B2

(12) United States Patent
Tsuji et al.

(10) Patent No.: US 12,734,282 B2
(45) Date of Patent: Sep. 15, 2026

(54) BLOOD PURIFICATION APPARATUS

(71) Applicant: NIKKISO CO., LTD., Tokyo (JP)

(72) Inventors: Kazuya Tsuji, Makinohara (JP); Takuya Maeda, Makinohara (JP); Hikaru Chiaki, Makinohara (JP)

(73) Assignee: NIKKISO CO., LTD., Tokyo (JP)

( * ) Notice: Subject to any disclaimer, the term of this patent is extended or adjusted under 35 U.S.C. 154(b) by 372 days.

(21) Appl. No.: 18/562,401

(22) PCT Filed: Mar. 22, 2022

(86) PCT No.: PCT/JP2022/013280
§ 371 (c)(1),
(2) Date: Nov. 20, 2023

(87) PCT Pub. No.: WO2022/264594
PCT Pub. Date: Dec. 22, 2022

(65) Prior Publication Data
US 2024/0245842 A1 Jul. 25, 2024

(30) Foreign Application Priority Data
Jun. 14, 2021 (JP) ................................ 2021-098770

(51) Int. Cl.
*A61M 1/30* (2006.01)
*A61M 60/109* (2021.01)
(Continued)

(52) U.S. Cl.
CPC ............ *A61M 1/30* (2013.01); *A61M 60/109* (2021.01); *A61M 60/216* (2021.01);
(Continued)

(58) Field of Classification Search
CPC ....................................................... A61M 1/14
See application file for complete search history.

(56) References Cited

U.S. PATENT DOCUMENTS

2003/0100857 A1 5/2003 Pedrazzi et al.
2008/0093276 A1* 4/2008 Roger .................... A61M 1/28
210/104

(Continued)

FOREIGN PATENT DOCUMENTS

JP 4160754 B2 10/2008
JP 6437349 B2 12/2018

OTHER PUBLICATIONS

Notification Concerning Transmittal of International Preliminary Report on Patentability (Chapter I of the Patent Cooperation Treaty) issued on Dec. 28, 2023, in corresponding International Application No. PCT/JP2022/013280, 5 pages.

(Continued)

*Primary Examiner* — Adam Marcetich
*Assistant Examiner* — Ted Yang
(74) *Attorney, Agent, or Firm* — Maier & Maier, PLLC

(57) ABSTRACT

In draining liquid in an AV-coupling-type blood circuit, it is determined that the blood circuit is in an AV-coupled state. A blood purification apparatus can switch between an open state in which fluid can flow through a blood removal side circuit and a blood return side circuit and a closed state in which the fluid cannot flow therethrough. The apparatus generates a difference in pressure between the blood removal side circuit and the blood return side circuit by rotating a blood pump in the case of the closed state. The apparatus then determines whether the blood circuit is the closed circuit by switching to the open state and monitoring the difference in pressure from detecting pressure inside the blood circuit. The apparatus drains liquid remaining in the blood circuit to a predetermined drainage destination with the blood circuit forming the closed circuit.

9 Claims, 13 Drawing Sheets

(51) Int. Cl.
*A61M 60/216* (2021.01)
*A61M 60/408* (2021.01)
*A61M 60/508* (2021.01)

(52) U.S. Cl.
CPC ........ *A61M 60/408* (2021.01); *A61M 60/508* (2021.01); *A61M 2205/3331* (2013.01)

(56) References Cited

U.S. PATENT DOCUMENTS

2010/0326916 A1* 12/2010 Wrazel ................ A61M 1/1686 210/205
2011/0192796 A1* 8/2011 Smejtek .................. A61M 1/14 210/652
2014/0276376 A1* 9/2014 Rohde ................ A61M 1/1605 604/29
2017/0095602 A1* 4/2017 Ishizaki .................. A61M 1/16
2017/0173253 A1* 6/2017 Funkhouser ........ A61M 1/3656
2017/0361003 A1 12/2017 Toyoda et al.
2018/0093027 A1* 4/2018 Oppegard ........... A61M 1/1601
2018/0117232 A1* 5/2018 Boylan ................. F04B 43/073
2018/0117233 A1* 5/2018 Boylan ................... A61M 1/14
2019/0209766 A1* 7/2019 Thiebaud ............ A61M 1/1561
2023/0040372 A1* 2/2023 Vartia ................ A61M 1/1672

OTHER PUBLICATIONS

Notification of Transmittal of Translation of the International Preliminary Report on Patentability (Chapter I or Chapter II of the Patent Cooperation Treaty) issued on Dec. 28, 2023, in corresponding International Application No. PCT/JP2022/013280, 5 pages.

* cited by examiner

| STATE | | S201 V PRESSURE SENSOR CONFIRMATION | S203 A SIDE REDUCED IN PRESSURE | S204 A SIDE REMAINED AT NEGATIVE PRESSURE | S206 AV COUPLING CONFIRMATION |
|---|---|---|---|---|---|
| NORMAL (AV COUPLED STATE) | V PRESSURE | ↗ | → | → | ↘ |
| | A PRESSURE | → | ↘ | → | ↗ |
| ABNORMAL (AV CONNECTED TO PATIENT) | V PRESSURE | ↗ | → | → | — |
| | A PRESSURE | → | ↘ | ↗ Fail | — |
| ABNORMAL (A SIDE OPEN, V SIDE CONNECTED TO PATIENT) | V PRESSURE | ↗ | → | → | — |
| | A PRESSURE | → | → | → Fail | — |
| ABNORMAL (A SIDE CLOSED, V SIDE CONNECTED TO PATIENT) | V PRESSURE | ↗ | → | → | → Fail |
| | A PRESSURE | → | ↘ | → | → Fail |

FIG.8

BLOOD PURIFICATION APPARATUS

FIELD

The present invention relates to a blood purification apparatus that self-evaluates the connection state of a blood circuit in draining liquid in the blood circuit.

BACKGROUND

A blood purification apparatus can be used in treating a patient. A blood purification apparatus has a blood circuit for removing blood from the body of a patient and returning blood into the body again. The blood circuit is mainly formed of a blood removal circuit (also called an arterial side circuit) and a blood return circuit (also called a venous side circuit) that may be connected to a dialyzer. The dialyzer is known as a blood purifier.

After treatment of a patient, puncture needles are pulled out of the body of the patient, and liquid in the blood circuit is drained and disposed of. The reason for this practice is to, in a case where liquid is remaining in the blood circuit, prevent a healthcare worker doing later work from being exposed to the liquid and the like and to reduce the disposal cost for disposal of the blood circuit and the dialyzer (Patent Literature 1).

PATENT LITERATURES

PTL 1: Japanese Patent No. 4160754

PTL 2: Japanese Patent No. 6437349

SUMMARY

Patent Literature 1 discloses a method for draining liquid in a blood circuit hygienically and safely for a patient by making the blood circuit a closed loop. However, Patent Literature 1 does not address a method for checking the connection state of the blood circuit before starting drainage of liquid in the blood circuit. In a case where drainage is done without a proper closed circuit being formed, leakage of liquid from the blood circuit occurs, and in a case where the patient is still connected, unnecessary blood removal may be performed. In this way, problematically, drainage may be performed improperly.

A process of draining liquid in a blood circuit of an AV-coupling type (closed loop) is performed with no needles being punctured in the patient and with the blood removal circuit and the blood return circuit being coupled, i.e., in an AV coupled state. Patent Literature 2 discloses a method for stopping a blood pump and restricting the operation to a low-speed operation in a case where there is a possibility of a needle being connected to a patient in a process before drainage of liquid in the blood circuit is performed. However, Patent Literature 2 does not address determination of the AV coupled state.

The present invention aims to determine if the blood circuit is in the AV coupled state in performing drainage of liquid in the blood circuit.

A blood purification apparatus according to an aspect of the present invention includes: a blood circuit having a blood removal side circuit into which blood removed from a patient flows and a blood return side circuit from which blood is returned to the patient and being able to form a closed circuit by having a first end portion of the blood removal side circuit and a first end portion of the blood return side circuit connected to each other via a blood purifier and by having a second end portion of the blood removal side circuit and a second end portion of the blood return side circuit connected to each other directly or indirectly; a blood pump provided at the blood circuit; a flow channel switch unit capable of switching between an open state in which fluid is able to flow through the first end portions of the blood removal side circuit and the blood return side circuit and a closed state in which the fluid is unable to flow through the first end portions of the blood removal side circuit and the blood return side circuit; a pressure detection unit that detects pressure inside the blood circuit; and a control unit that executes a drainage process of draining liquid remaining in the blood circuit to a predetermined drainage destination with the blood circuit forming the closed circuit. The control unit further executes a determination process in which the control unit generates a difference in pressure between the blood removal side circuit and the blood return side circuit by rotating the blood pump with the flow channel switch unit switched to the closed state, and then determines whether the blood circuit is the closed circuit by switching the flow channel switch unit to the open state and monitoring the difference in pressure based on a result of detection by the pressure detection unit. In a case where it is determined in the determination process that the blood circuit is the closed circuit, the control unit executes the drainage process after the determination.

The blood purification apparatus can self-evaluate that the blood circuit is in an AV coupled state in performing drainage of liquid in the AV-coupling-type blood circuit.

BRIEF DESCRIPTION OF DRAWINGS

In-depth understanding of embodiments disclosed herein can be gained from the following description exemplified in relation to the drawings attached hereto.

FIG. 8 is a diagram showing lists of A pressures and V pressures in the first to fourth states.

DETAILED DESCRIPTION

Blood purification apparatuses according to some embodiments are described below with reference the drawings attached hereto. Although a blood purification apparatus can be a device used for dialysis treatment, the gist of the present invention can also be applied to devices other than ones for dialysis treatment. A blood purification apparatus includes a piping unit for allowing a dialysate to flow into a dialyzer and an extracorporeal circulation unit for allowing the blood of a patient to flow into the dialyzer. Herein, the gist of the present invention is described with reference to the configuration of the extracorporeal circulation unit of the blood purification apparatus.

Herein, an artery may be referred to as “A” based on the initial letter of the English word, and a vein may be referred to as “V” based on the initial letter of the English word. For instance, “arterial side . . . ” may be written as “A side . . . ,” and “venous side . . . ” may be written as “V side . . . ” Also, the term “drainage process” used herein means a process of draining liquid in the blood circuit.

(First Embodiment) (Overall Configuration)

Figure 1:
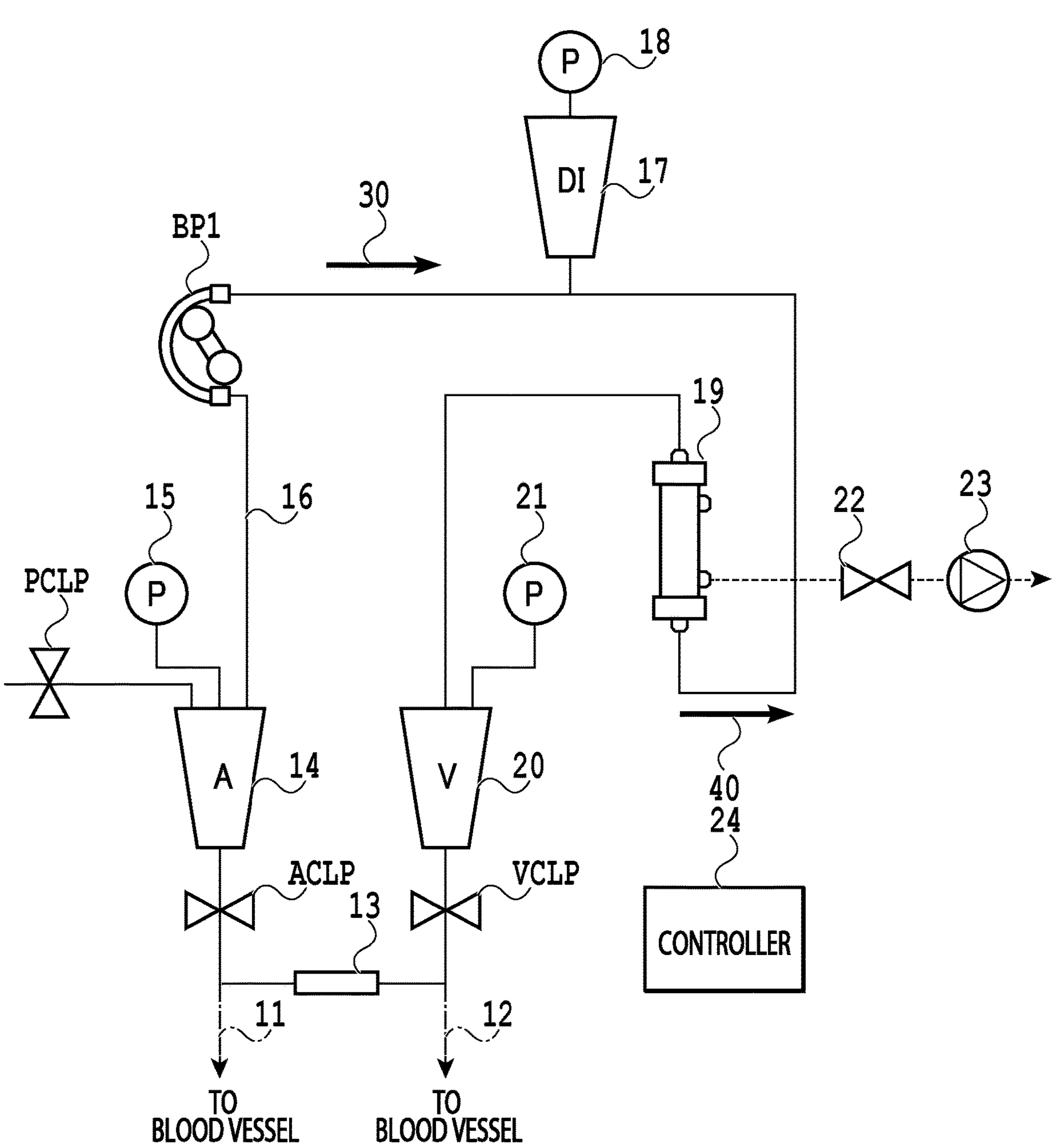
FIG. 1 is a piping diagram showing the configuration of a blood purification apparatus according to a first embodiment.

FIG. 1 is a piping diagram showing the configuration of a blood purification apparatus 100 according to a first embodiment. FIG. 1 shows that a blood removal circuit can be connected to a blood vessel of a patient at a patient connection portion 11 of the blood removal circuit and that a blood return circuit can be connected to a blood vessel of the patient at a patient connection portion 12 of the blood return circuit. After the patient is treated, the patient connection portion 11 of the blood removal circuit and the patient connection portion 12 of the blood return circuit are pulled out of the body of the patient and are coupled to each other so that a blood circuit 16 may be a closed loop. The patient connection portion 11 and the patient connection portion 12 may be coupled to each other via a given coupler. This is called an AV coupled state 13 herein.

The blood purification apparatus 100 includes an arterial clamp (ACLP), an A chamber 14, a priming line clamp (PCLP), an A pressure sensor 15, the blood circuit 16, a blood pump (BP1), a DI chamber 17, a DI pressure sensor 18, a blood purifier 19, a V chamber 20, a V pressure sensor 21, a venous clamp (VCLP), a solenoid valve 22, a drainer 23, and a controller 24. The controller 24 controls the operation of the blood purification apparatus 100 described herein. Note that the controller 24 is configured by appropriately combining a CPU, a ROM, a RAM, and various interfaces.

The ACLP is a clamp attached to the blood removal circuit, and the VCLP is a clamp attached to the blood return circuit. The PCLP is a clamp attached to a line (a priming line) for introducing a dialysate, a physiological saline solution, or the like into the blood circuit 16 at the time of, e.g., priming of the blood circuit 16. The clamp may be a solenoid valve that closes or opens the blood circuit 16 by opening and closing operations.

The A chamber 14 traps air in the blood removal circuit. The DI chamber 17 traps air in the blood flowing to the blood purifier 19. The V chamber 20 traps air in the blood return circuit.

The A pressure sensor 15 is a pressure sensor for measuring the pressure inside the blood circuit 16 at the A chamber 14. The DI pressure sensor 18 is a pressure sensor for measuring the pressure inside the blood circuit 16 at the DI chamber 17. The V pressure sensor 21 is a pressure sensor for measuring the pressure inside the blood circuit 16 at the V chamber 20.

The BP1 can send the blood, physiological saline solution, and air in the blood circuit 16 in a predetermined direction. As the BP1 rotates forwards, the blood, physiological saline solution, and air flow in the blood circuit 16 in a first direction 30, and as the BP1 rotates backwards, the blood, physiological saline solution, and air flow in the blood circuit 16 in a second direction 40 which is opposite from the first direction 30. Herein, the forward rotation means clockwise rotation, and the backward rotation means counterclockwise rotation.

The blood purifier 19 may be called a dialyzer. The blood purifier 19 has a blood purification membrane thereinside and also has a blood introduction inlet for introducing blood, a blood introduction outlet for letting out the introduced blood, a dialysate introduction inlet for introducing a dialysate, and a dialysate drainage outlet for draining the introduced dialysate. The blood purifier 19 purifies the blood introduced from the blood introduction inlet by bringing it into contact with the dialysate via the blood purification membrane.

The drainer 23 is a degassing pump or water removal pump that drains waste and moisture in the blood sent via a drainage circuit from the blood purifier 19. The drainage circuit is a circuit connecting between the blood purifier 19 and the drainer 23 and shown with a broken line in FIG. 1. The solenoid valve 22 is attached between the blood purifier 19 and the drainer 23 and closes or opens the drainage circuit by opening and closing operations.

To perform drainage of liquid in the AV-coupling-type blood circuit, the patient connection portion 11 of the blood removal circuit and the patient connection portion 12 of the blood return circuit need to be coupled either indirectly via a given coupler or directly without any coupler to make the blood circuit 16 a closed loop. Performing a drainage process with the blood circuit 16 connected to the patient, i.e., not in the AV coupled state 13, poses a risk for the blood purification apparatus 100 to send air or liquid remaining in the blood circuit to the patient and perform blood removal subsequently. Also, even if the blood circuit 16 is pulled out of the patient, in a case where the AV coupled state 13 is not established, there is a possibility that liquid remaining in the blood circuit may leak out from the patient connection portion 11 of the blood removal circuit and/or the patient connection portion 12 of the blood return circuit due to introduction of air into the blood circuit 16 from the priming line or a different location or due to rotation of the BP1.

(Self-Evaluation Operation Flow)

An operation flow of self-evaluation according to the first embodiment carried out in starting drainage of liquid in the AV-coupling-type blood circuit is described below with reference to FIG. 2. The self-evaluation is performed to confirm that the blood circuit 16 is in the AV coupled state 13, i.e., in a closed-loop state.

In S201, the blood purification apparatus 100 determines if the V pressure sensor 21 and the blood circuit 16 are connected. Specifically, the blood purification apparatus 100 closes the ACLP, the VCLP, and the solenoid valve 22, opens the PCLP to introduce air, physiological saline solution, or dialysate from the priming line, and rotates the BP1 forwards. This operation causes the V side to have increased pressure.

Figure 3:
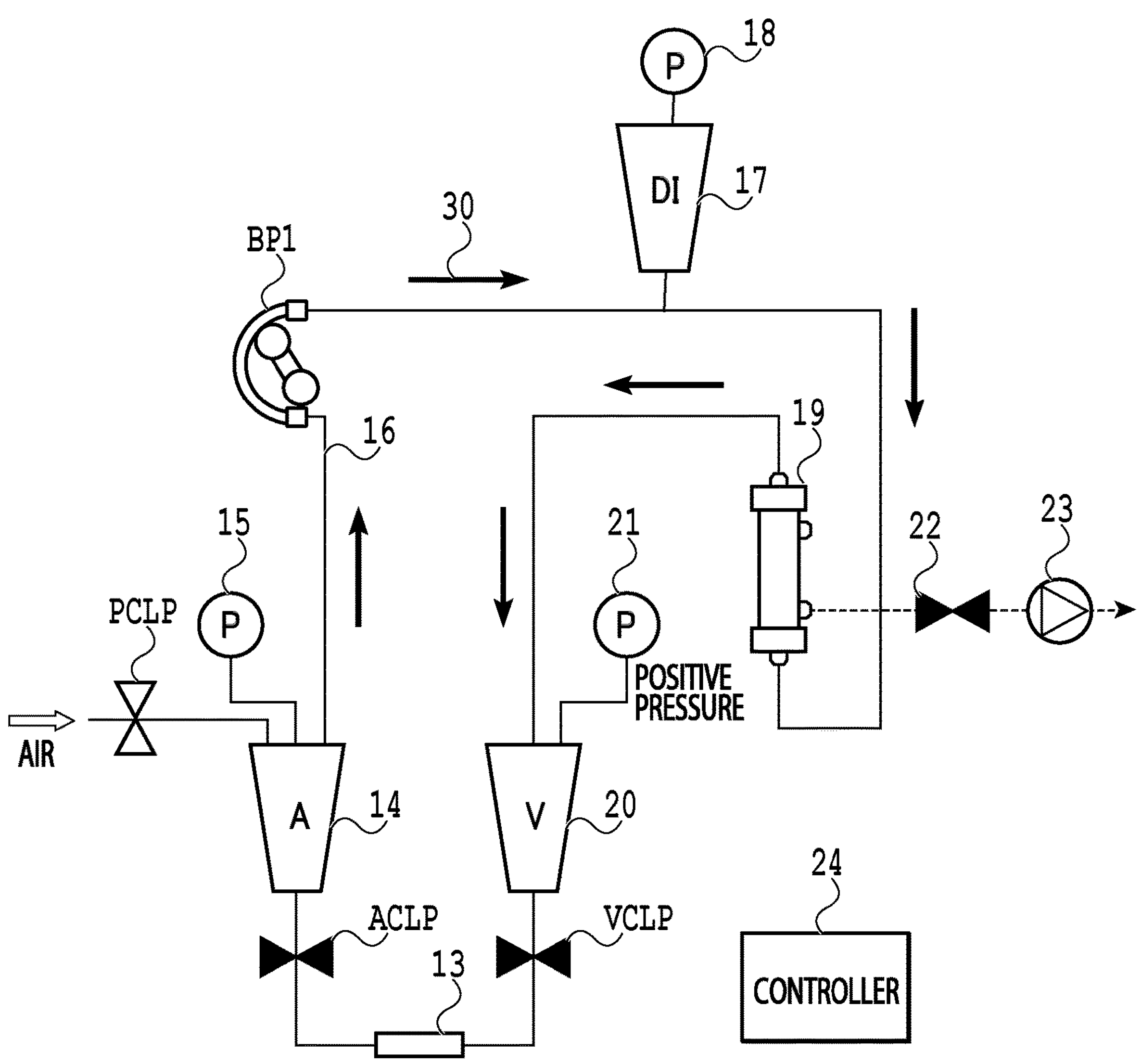
FIG. 3 is a diagram showing a first state of the blood purification apparatus according to the first embodiment.

FIG. 3 is a diagram showing this state (a first state). Because the ACLP, the VCLP, and the solenoid valve 22 are closed, they are shown distinguishably from the PCLP. Because the BP1 is rotating forwards, the introduced air, physiological saline solution, or dialysate travels in the blood circuit 16 along the arrows indicating the first direction 30. In FIG. 3, the direction in which the air, physiological saline solution, or dialysate travels is shown with a plurality of arrows. As a result of this operation, the V side is brought to positive pressure.

Reasons for closing the ACLP and the VCLP are to eliminate the risk of bubbles entering the patient even in a case where the blood return circuit is connected to the patient and also to prevent blood removal in a case where the blood removal circuit is connected to the patient.

In S202, if it is determined that the V side is under increased pressure, the blood purification apparatus 100 determines that the V pressure sensor 21 and the blood circuit 16 are connected, and the processing proceeds to S203. A predetermined criterion can be used as a criterion for determining whether the V side is under increased pressure. If it is determined that the V side is not under increased pressure, it is determined that the V pressure sensor 21 and the blood circuit 16 are not connected, and the processing proceeds to S209.

In S203, the blood purification apparatus 100 determines if the A side is not connected to the patient. The reason for performing this determination is because if the blood removal circuit is connected to the patient, then blood will be removed from the patient. Specifically, the blood purification apparatus 100 closes the PCLP, opens the ACLP and the solenoid valve 22, and then rotates the BP1 forwards. Unlike the processing in S201, because the PCLP is closed, air, physiological saline solution, or dialysate is not introduced into the blood circuit 16, and the A side is brought to negative pressure.

Figure 4:
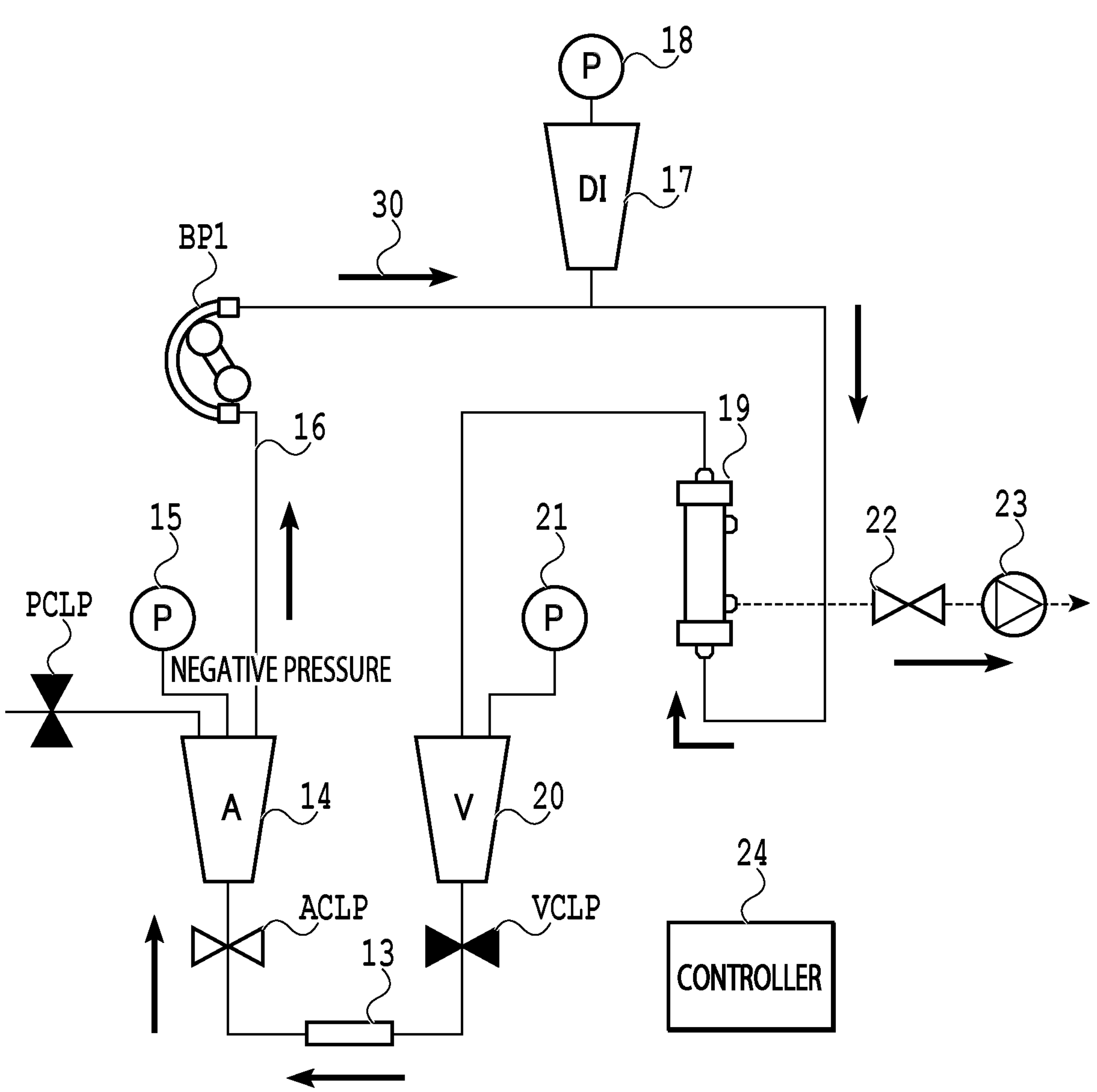
FIG. 4 is a diagram showing a second state of the blood purification apparatus according to the first embodiment.

FIG. 4 is a diagram showing this state (a second state). FIG. 4 shows that the BP1 is rotating forwards and the A side is under negative pressure.

Because the V pressure is increased by the forward rotation of the BP1, the blood purification apparatus 100 can reduce the pressure of the downstream side (the V side) by opening the solenoid valve 22.

In S204, the blood purification apparatus 100 determines if the A side is not connected to the patient. Specifically, the blood purification apparatus 100 closes the solenoid valve 22, stops the rotation of the BP1, and measures a change in the A pressure afterwards using the A pressure sensor 15. The BP1 is a roller pump, and once the BP1 is stopped, the BP1 part is closed, making the part from the VCLP to the ACLP to the BP1 a closed circuit and keeping the A side under negative pressure. Any given condition can be set as the condition for the A side being under negative pressure, and the condition may be such that a change in the A pressure in a predetermined period of time after the BP1 is stopped falls within a predetermined range.

Figure 5:
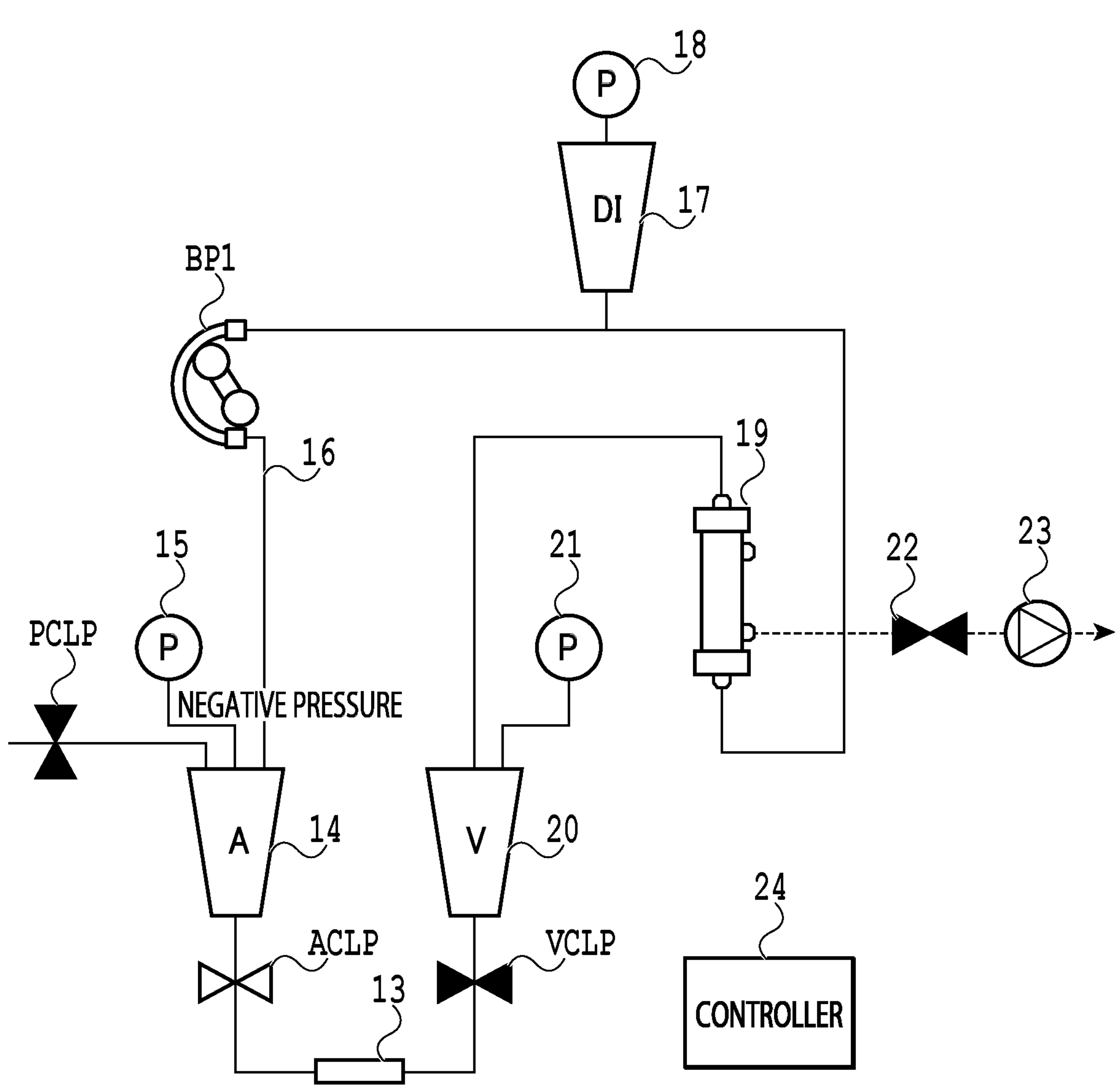
FIG. 5 is a diagram showing a third state of the blood purification apparatus according to the first embodiment.

FIG. 5 is a diagram showing this state (a third state). While the ACLP is open, the PCLP and the VCLP are still closed, and the BP1 is stopped; thus, the A side pressure remains under negative pressure.

In S205, if the A side pressure remains under negative pressure, it is determined that the A side is not connected to the patient, and the processing proceeds to S206. Meanwhile, if the A side pressure is no longer under negative pressure, it is determined that the A side is connected to the patient or that an atmosphere relief state is established, and the processing proceeds to S209. Note that if the A side is connected to the patient, blood may be removed from the body of the patient, but the controller 24 may be configured to restrict the amount of rotation of the BP1 in S203 to minimize the blood removal.

In S206, the blood purification apparatus 100 determines if the A side and the V side of the blood circuit 16 are coupled and the AV coupled state 13 is established. Specifically, the blood purification apparatus 100 brings the ACLP and the VCLP into an open state by opening the VCLP, measures the A pressure and the V pressure using the A pressure sensor 15 and the V pressure sensor 21, respectively, and compares the pressure difference between them. The PCLP and the solenoid valve 22 are still closed. The condition for establishment of the AV coupled state 13 is, for example, the difference between the A pressure and the V pressure becoming so small as to fall within a predetermined range. The reason for bringing the ACLP and the VCLP into an open state is to balance (equalize) the pressures at the A side and the V side.

Figure 6:
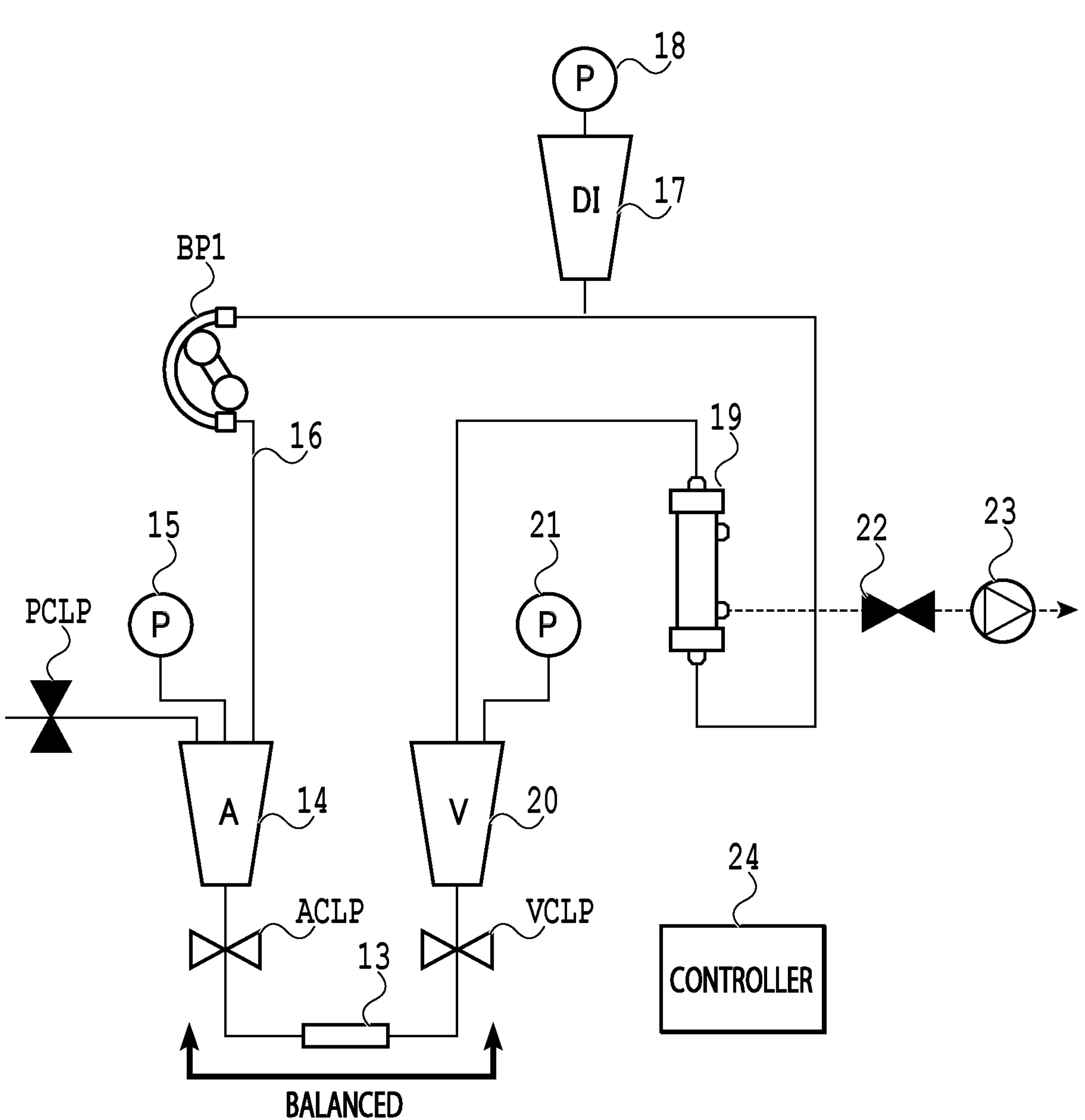
FIG. 6 is a diagram showing a fourth state of the blood purification apparatus according to the first embodiment.

FIG. 6 is a diagram showing this state (a fourth state). Because the BP1 is stopped, the residual liquid moves so as to balance the pressures at the A side and the V side. In this state, the blood purification apparatus 100 determines whether the condition for establishment of the AV coupled state 13 is satisfied by measuring the A pressure and the V pressure using the A pressure sensor 15 and the V pressure sensor 21, respectively, and comparing the pressure difference between them.

In S207, if it is determined that the AV coupled state 13 is established, the processing proceeds to S208, and if it is determined that the AV coupled state 13 is not established, the processing proceeds to S209.

In a case where the processing proceeds to S208, it means that before performing drainage of liquid in the AV-coupling-type blood circuit, the blood purification apparatus 100 has successfully self-evaluated that the blood circuit 16 is in the AV coupled state 13 (a closed loop state) as a result of the above-described processing.

Figure 7:
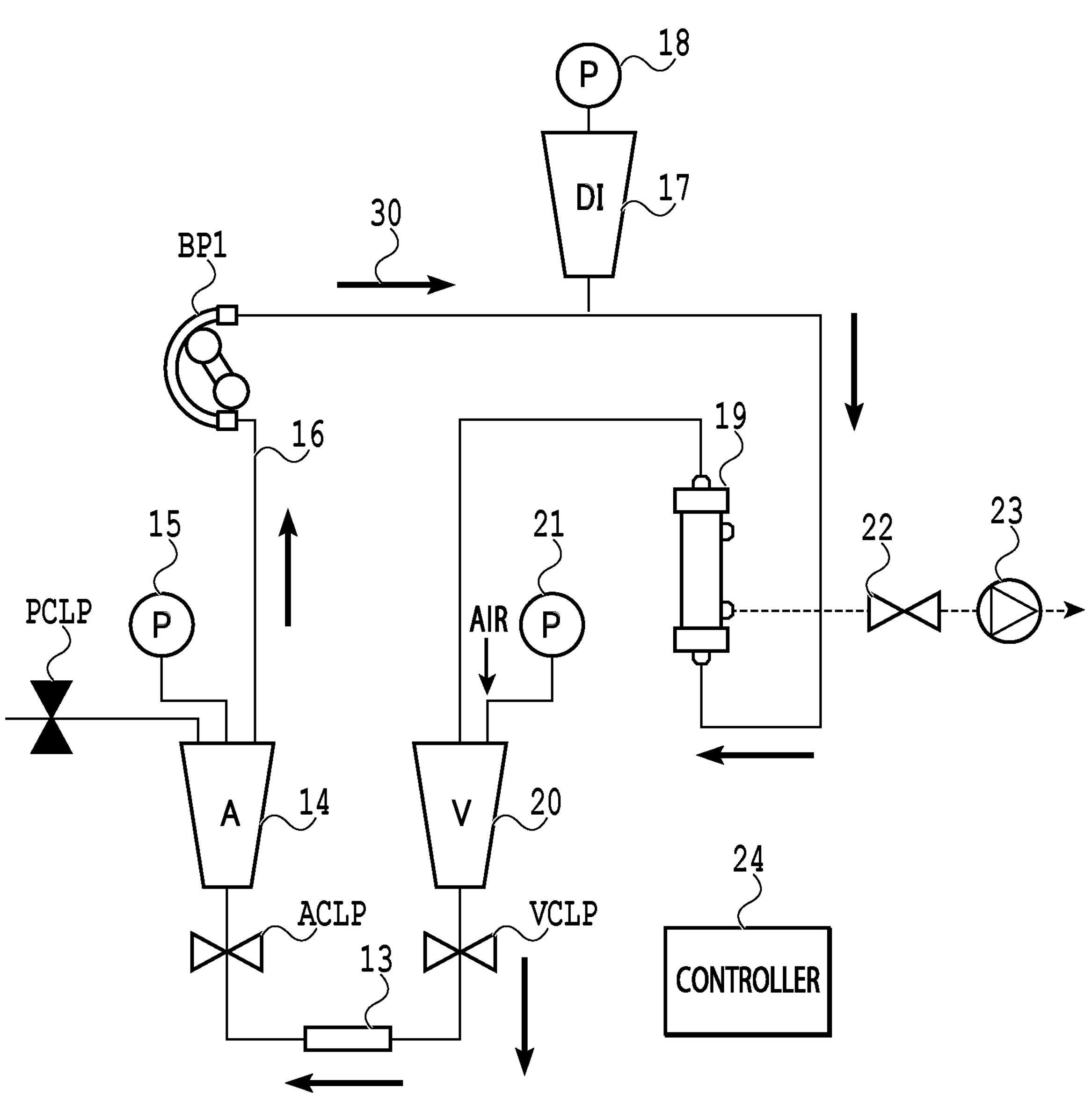
FIG. 7 is a diagram illustrating an operation of how liquid is drained from the blood circuit in an AV coupled state.

In S208, with the PCLP being closed and the solenoid valve 22, the ACLP, and the VCLP being open, the blood purification apparatus 100 starts an operation for draining liquid in the AV-coupling-type blood circuit. FIG. 7 is a diagram illustrating the operation for draining liquid from the blood circuit 16 in the AV coupled state 13. The blood purification apparatus 100 introduces air from an upper portion of the V chamber 20, an upper portion of the A chamber 14, or a given opening portion of the blood circuit 16 (such as, e.g., the PCLP or an upper portion of the DI chamber 17) and rotates the BP1 forwards. Once the BP1 rotates forwards, liquid remaining in the blood circuit 16 flows in the first direction 30 and is drained from the drainer 23 via the blood purifier 19, as shown in FIG. 7.

Note that in one embodiment of the present invention, in performing the drainage operation in S208, the blood purification apparatus 100 may control the amount of rotation of the BP1 in any given way. For example, the blood purification apparatus 100 can start rotating the BP1 while restricting the rotation amount to a first rotation amount and then after a predetermined period of time passes, increase the rotation amount to a second rotation amount. A reason for controlling the rotational amount of the BP1 this way is to reduce the amount of blood removed from the body of the patient, should the blood removal circuit be connected to the patient.

Figure 2:
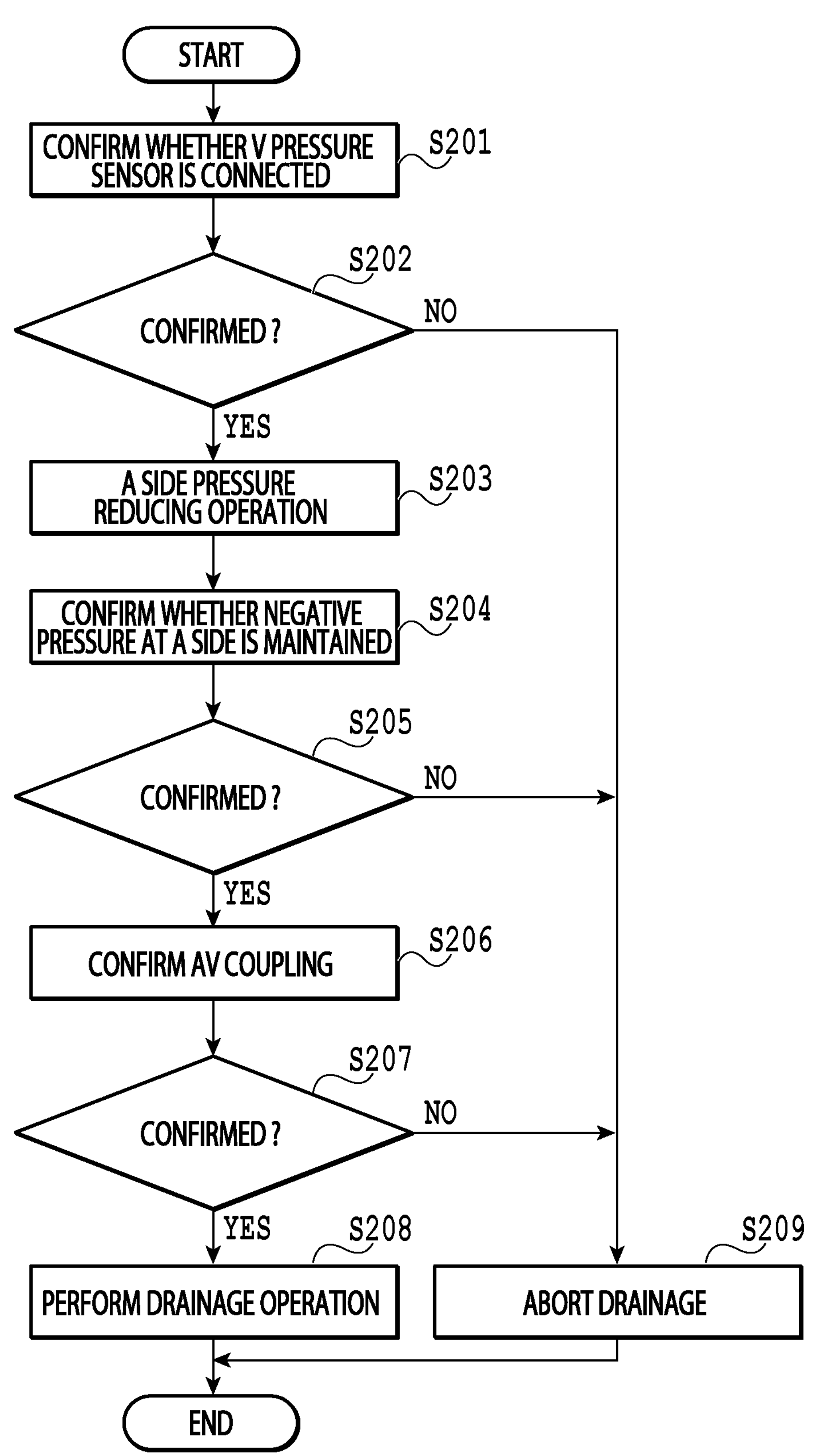
FIG. 2 is a diagram illustrating an operation flow of self-evaluation according to the first embodiment carried out in starting drainage of liquid in an AV-coupling-type blood circuit.

Although in the operation flow described with FIG. 2, the drainage operation is performed after it is determined that the blood circuit 16 is a closed loop, the present invention is not limited to this embodiment. The blood purification apparatus 100 can also be configured to start the drainage operation, and then in a case where it is determined that the blood circuit 16 is a closed loop, continue the drainage operation, or in a case where the blood circuit 16 is not a closed loop, abort the drainage operation at that point.

In a case where the processing proceeds to S209, it means that some trouble is occurring for the reasons described earlier, and thus, in S209, the blood purification apparatus 100 aborts the operation for draining liquid in the blood circuit 16.

FIG. 8 is a diagram showing lists of the A pressures and the V pressures in the first to fourth states. In a normal AV coupled state 13, the V pressure increases in S201 and then reduces in S206, while the A pressure reduces in S203 and increases in S206.

On the other hand, there are a plurality of conceivable cases where the connection state is abnormal. First, in a case where the A side and the V side are connected to the patient, the A pressure increases in S204, causing an error. Next, in a case where the A side is in an open state and the V side is connected to the patient, because air is introduced from the blood removal circuit, the A pressure does not change, causing an error. Lastly, in a case where the A side is in a closed state and the V side is connected to the patient, the V pressure remains increased and the A pressure remains reduced.

Second Embodiment

In the embodiment described as the first embodiment, the puncture needle of the patient connection portion 11 of the blood removal circuit and the puncture needle of the patient connection portion 12 of the blood return circuit are both connected to the patient. In the second embodiment, an SNDP (single-needle double-pump) configuration is described. Note that single-needle dialysis is a method for carrying out dialysis by having a route only at a single location on the patient and repeating blood removal and blood return alternately, and uses a special bifurcated needle or a bifurcated tube. Because liquid in the blood circuit may be drained and disposed of after a treatment in the single-needle approach as well, the self-evaluation method according to the present invention in performing drainage of liquid in the AV-coupling-type blood circuit can be applied.

The configuration of the second embodiment is such that a second blood pump (BP2), an SN chamber 25, and an SN pressure sensor 26 are added to the configuration of the first embodiment. The BP2 is a pump for increasing or reducing the pressure at the V side. The SN chamber 25 is formed of the same member as the A chamber 14, the DI chamber 17, and the V chamber 20 and plays the role as a buffer that accumulates pressure during a single-need treatment. The SN pressure sensor 26 is a pressure sensor for measuring the pressure inside the blood circuit 16 at the SN chamber 25. Referring to the configuration in FIG. 10, at the time of blood removal, the BP1 is rotated and the BP2 is stopped to accumulate pressure in the SN chamber 25, and at the time of blood return, the BP1 is stopped and the BP2 is rotated to return, to the patient, blood corresponding to the pressure accumulated in the SN chamber 25.

(Self-Evaluation Operation Flow)

Figure 9:
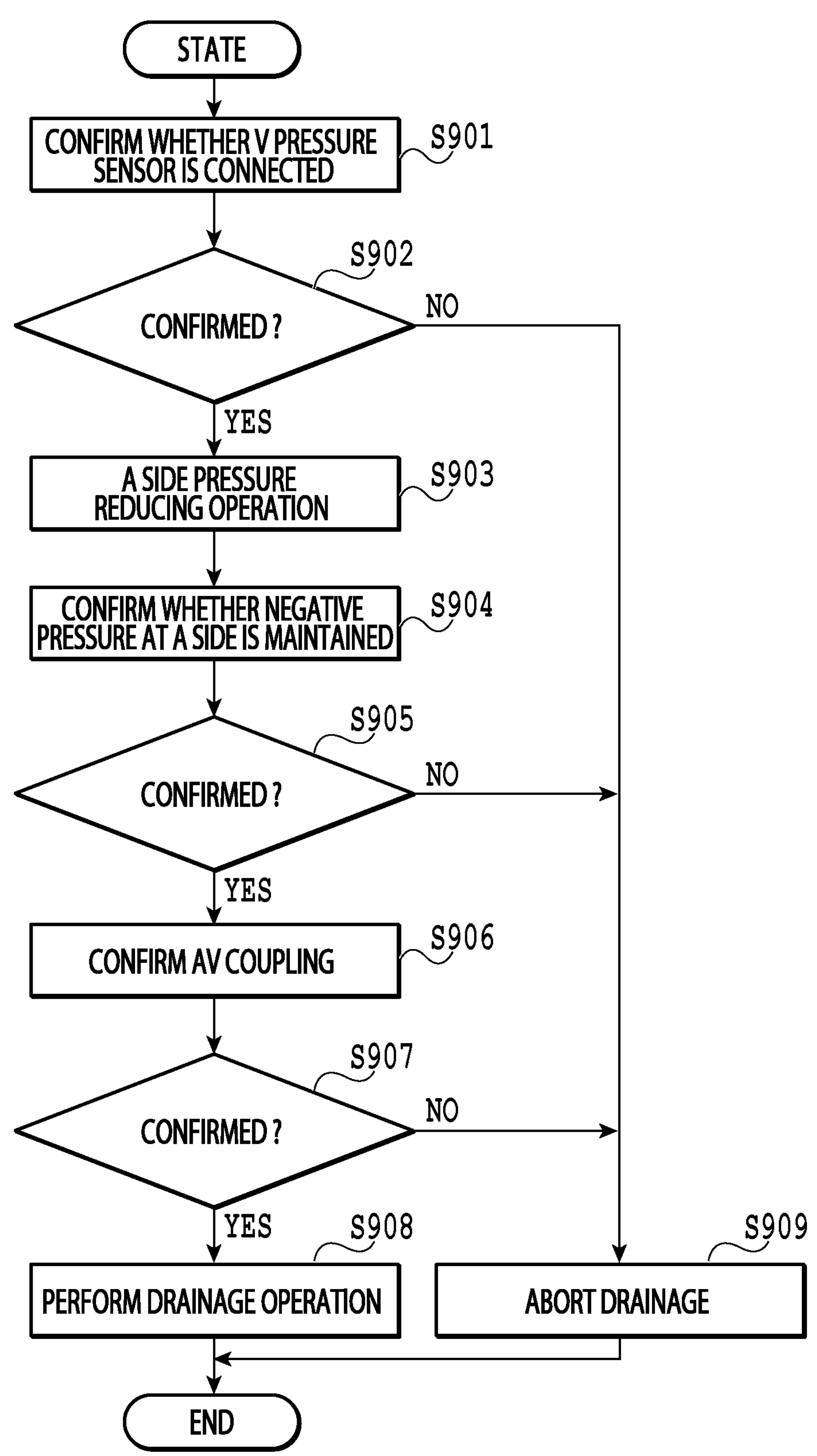
FIG. 9 is a diagram illustrating an operation flow of self-evaluation according to a second embodiment carried out in starting drainage of liquid in an AV-coupling-type blood circuit.

FIG. 9 is a diagram illustrating an operation flow of self-evaluation according to the second embodiment carried out in starting drainage of liquid in the AV-coupling-type blood circuit. The operation flow in FIG. 9 is similar to the operation flow described with FIG. 2. The self-evaluation is performed to confirm that the blood circuit 16 is in the AV coupled state 13, i.e., in a closed-loop state.

In S901, the blood purification apparatus 100 determines if the V pressure sensor 21 and the blood circuit 16 are connected. Specifically, the blood purification apparatus 100 closes the ACLP, the VCLP, and the solenoid valve 22 and opens the PCLP to introduce air, physiological saline solution, or dialysate from the priming line, and rotates the BP1 and the BP2 forwards. This operation causes the V side to be increased in pressure.

Figure 10:
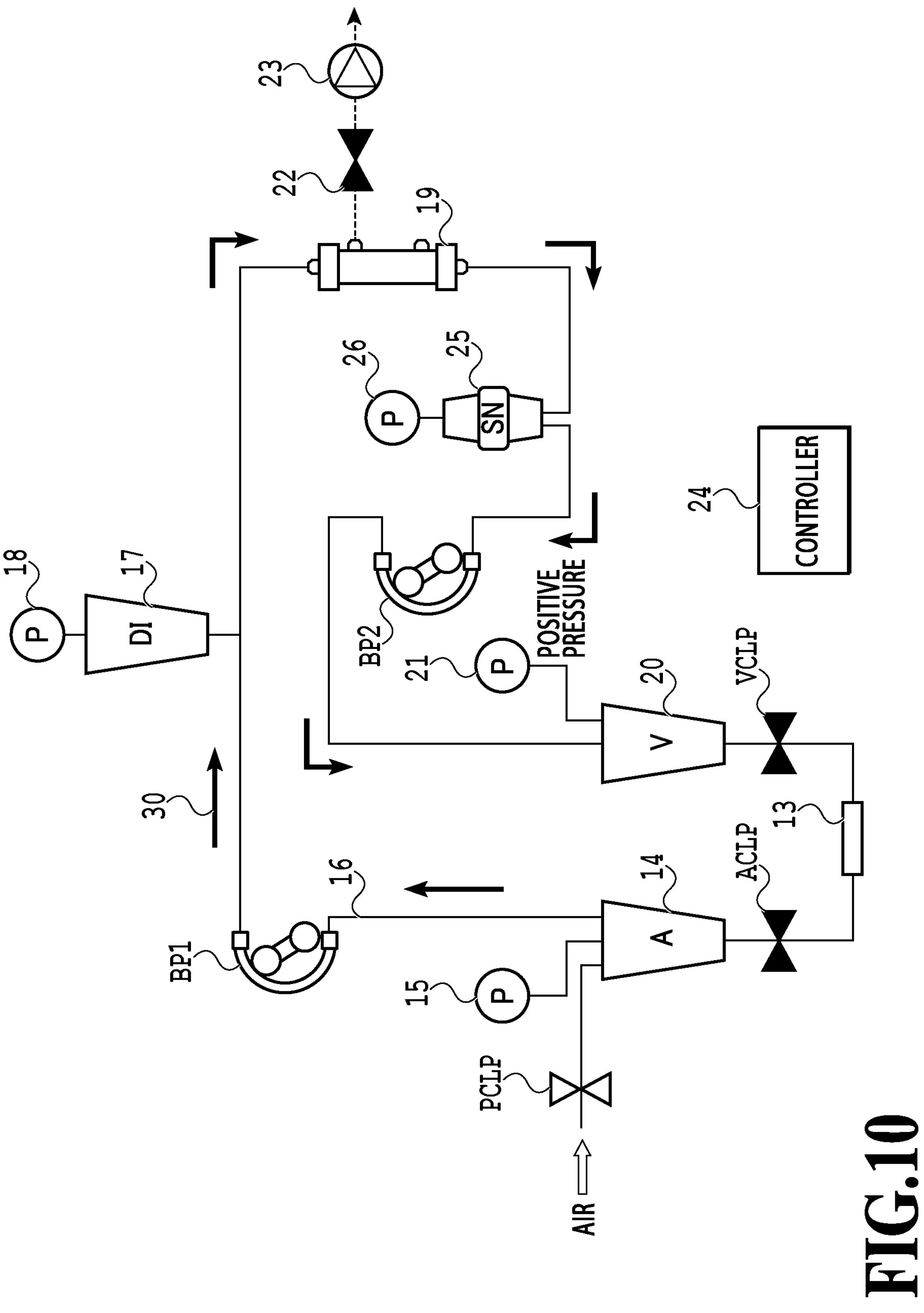
FIG. 10 is a diagram showing a fifth state of the blood purification apparatus according to the second embodiment.

FIG. 10 is a diagram showing this state (a fifth state). Because the ACLP, the VCLP, and the solenoid valve 22 are closed, they are shown distinguishably from the PCLP. Because the BP1 and the BP2 are rotating forwards, the introduced air, physiological saline solution, or dialysate travels in the blood circuit 16 along the arrows indicating the first direction 30. In FIG. 10, the direction in which the air, physiological saline solution, or dialysate travels is shown with a plurality of arrows. As a result of this operation, the V side is brought to positive pressure.

Reasons for closing the ACLP and the VCLP is to eliminate the risk of bubbles entering the patient even if the blood return circuit is connected to the patient and also to prevent blood removal in a case where the blood removal circuit is connected to the patient.

In S902, if it is determined that the V side is under increased pressure, the blood purification apparatus 100 determines that the V pressure sensor 21 and the blood circuit 16 are connected, and the processing proceeds to S903. A predetermined criterion can be used as a criterion for determining whether the V side is under increased pressure. On the other hand, if it is determined that the V side is not under increased pressure, it is determined that the V pressure sensor 21 and the blood circuit 16 are not connected, and the processing proceeds to S909.

In S903, the blood purification apparatus 100 determines if the A side is not connected to the patient. The reason for performing this determination is because if the blood removal circuit is connected to the patient, then blood will be removed from the patient. Specifically, the blood purification apparatus 100 closes the PCLP and opens the ACLP and the solenoid valve 22, and then rotates the BP1 forwards and the BP2 backwards. Unlike the processing in S901, because the PCLP is closed, air, physiological saline solution, or dialysate is not introduced into the blood circuit 16, and the A side is brought to negative pressure.

Figure 11:
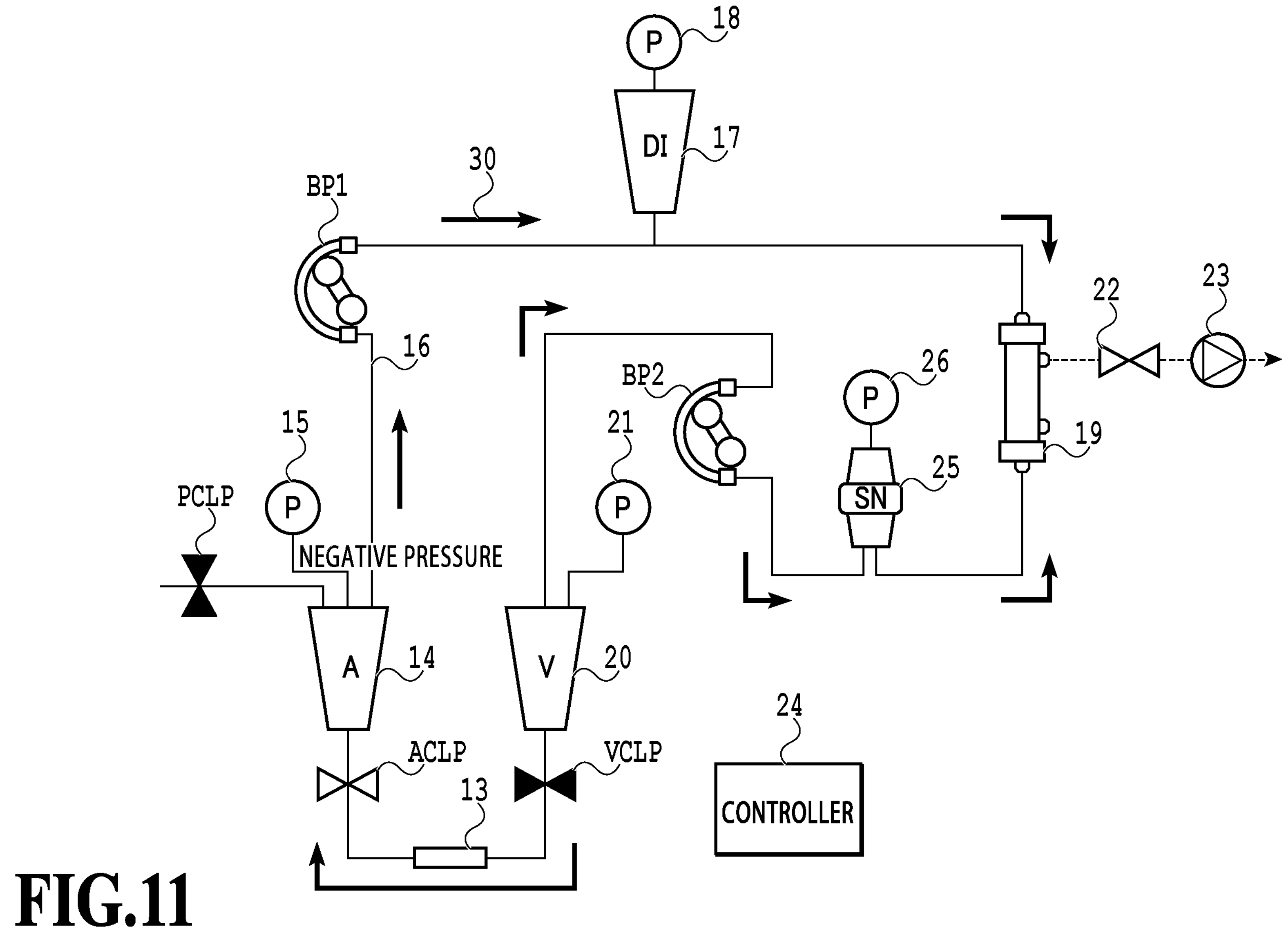
FIG. 11 is a diagram showing a sixth state of the blood purification apparatus according to the second embodiment.

FIG. 11 is a diagram showing this state (a sixth state). Because the BP1 is rotating forwards, the A side is under negative pressure. Also, because the BP2 is rotating backwards, the V side is reduced in pressure.

The forward rotation of the BP1 and the backward rotation of the BP2 cause the liquid such as blood remaining in the blood circuit 16 to be drained from the drainer 23 via the blood purifier 19 and the solenoid valve 22, and the V side is reduced in pressure.

In S904, the blood purification apparatus 100 determines if the A side is not connected to the patient. Specifically, the blood purification apparatus 100 closes the solenoid valve 22, stops the rotation of the BP1 and the BP2, and measures a change in the A pressure afterwards using the A pressure sensor 15. The BP1 is a roller pump, and once the BP1 is stopped, the BP1 part is closed, making the part from the VCLP to the ACLP to the BP1 a closed circuit and keeping the A side under negative pressure. Any given condition can be set as the condition for the A side being under negative pressure, and the condition may be such that a change in the A pressure in a predetermined period of time after the BP1 and the BP2 are stopped falls within a predetermined range.

Figure 12:
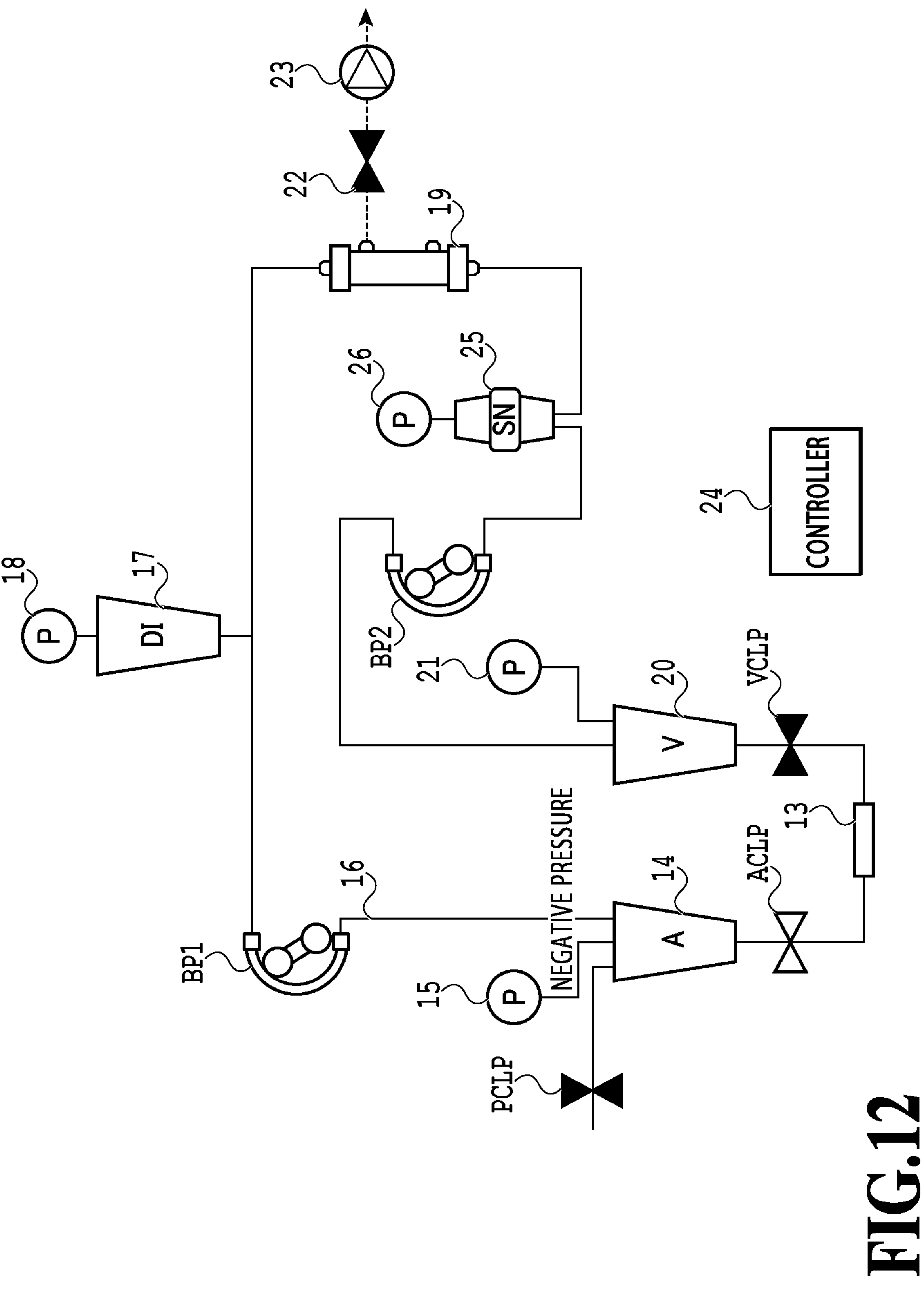
FIG. 12 is a diagram showing a seventh state of the blood purification apparatus according to the second embodiment.

FIG. 12 is a diagram showing this state (a seventh state). While the ACLP is open, the PCLP and the VCLP are still closed, and the BP1 is stopped; thus, the A side pressure is still under negative pressure.

In S905, if the A side pressure is still under negative pressure, it is determined that the A side is not connected to the patient, and the processing proceeds to S906. Meanwhile, if the A side pressure is no longer under negative pressure, it is determined that either the A side is connected to the patient or an atmosphere relief state is established, and the processing proceeds to S909. Note that if the A side is connected to the patient, blood may be removed from the body of the patient, but the controller 24 may be configured to restrict the amount of rotation of the BP1 and the BP2 in S903 to minimize the blood removal.

In S906, the blood purification apparatus 100 determines if the A side and the V side of the blood circuit 16 are coupled and the AV coupled state 13 is established. Specifically, the blood purification apparatus 100 brings the ACLP and the VCLP into an open state by opening the VCLP, measures the A pressure and the V pressure using the A pressure sensor 15 and the V pressure sensor 21, respectively, and compares the pressure difference between them. The PCLP and the solenoid valve 22 are still closed. The condition for establishment of the AV coupled state 13 is, for example, the difference between the A pressure and the V pressure becoming so small as to fall within a predetermined range. The reason for bringing the ACLP and the VCLP into an open state is to balance (equalize) the pressures at the A side and the V side.

Figure 13:
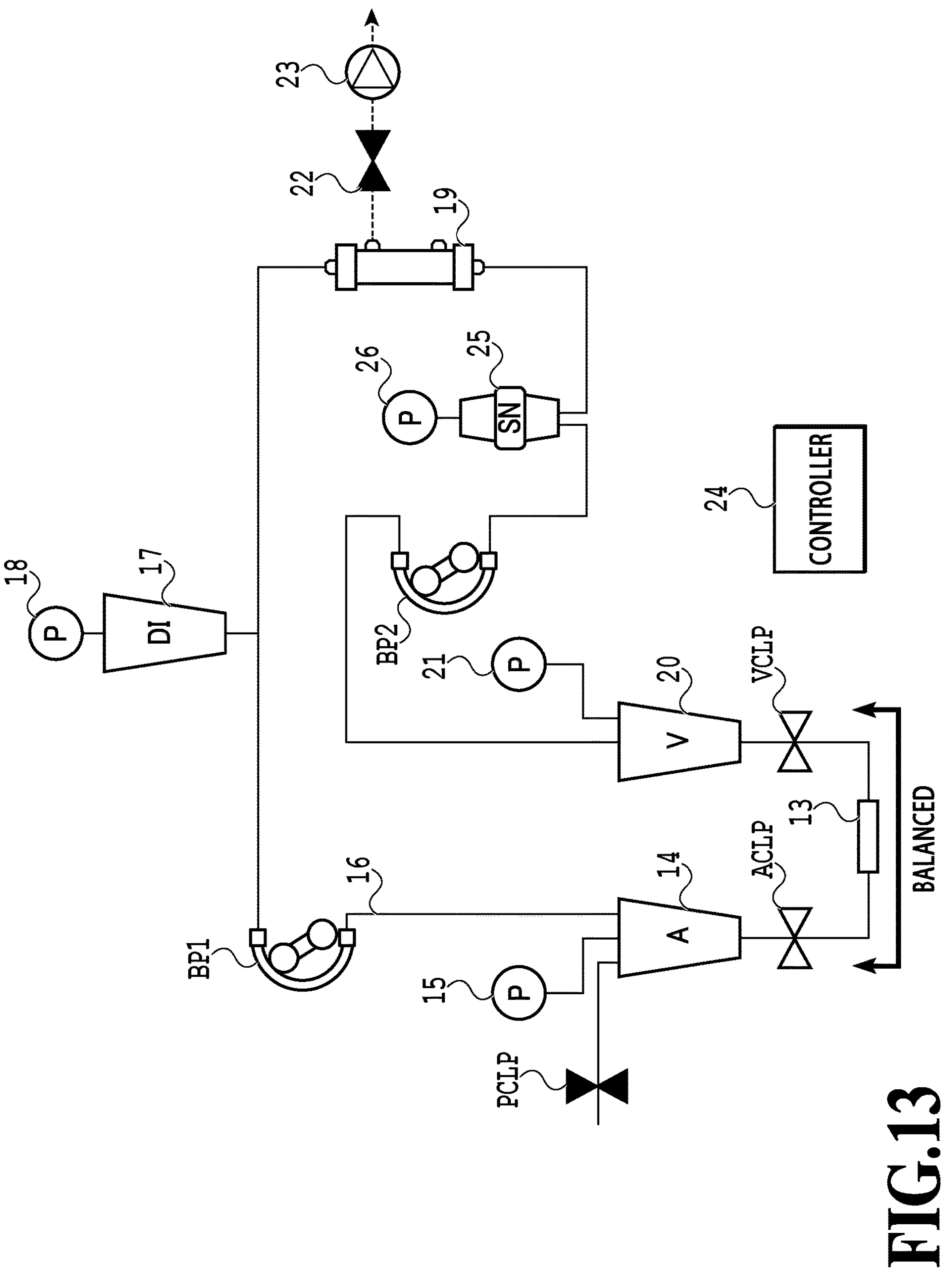
FIG. 13 is a diagram showing an eighth state of the blood purification apparatus according to the second embodiment.

FIG. 13 is a diagram showing this state (an eighth state). Because the BP1 and the BP2 are stopped, the residual liquid moves to balance the pressures at the A side and the V side. In this state, the blood purification apparatus 100 determines whether the condition for establishment of the AV coupled state 13 is satisfied by measuring the A pressure and the V pressure using the A pressure sensor 15 and the V pressure sensor 21, respectively, and comparing the pressure difference between them.

In S907, if it is determined that the AV coupled state 13 is established, the processing proceeds to S908, and if it is determined that the AV coupled state 13 is not established, the processing proceeds to S909.

In a case where the processing proceeds to S908, it means that before performing drainage of liquid in the AV-coupling-type blood circuit, the blood purification apparatus 100 has successfully self-evaluated that the blood circuit 16 is in the AV coupled state 13 (a closed loop state) as a result of the above-described processing.

In S908, with the PCLP being closed and the solenoid valve 22, the ACLP, and the VCLP being open, the blood purification apparatus 100 starts an operation for draining liquid in the AV-coupling-type blood circuit. The blood purification apparatus 100 introduces air from an upper portion of the V chamber 20, an upper portion of the A chamber 14, or a given opening portion of the blood circuit 16 (such as, e.g., the PCLP or an upper portion of the DI chamber 17) and rotates the BP1 forwards and the BP2 backwards. Once the BP1 rotates forwards, liquid remaining in the blood removal circuit flows in the first direction 30, liquid remaining in the blood return circuit flows in the second direction 40, and the liquid is drained from the drainer 23 via the blood purifier 19.

Note that in one embodiment of the present invention, in performing the drainage operation in S908, the blood purification apparatus 100 may control the amount of rotation of the BP1 in any given way. For example, the blood purification apparatus 100 can start rotating the BP1 while restricting the rotation amount to a first rotation amount and then after a predetermined period of time passes, increase the rotation amount to a second rotation amount. A reason for controlling the rotational amount of the BP1 this way is to reduce the amount of blood removed from the body of the patient, should the blood removal circuit be connected to the patient.

Although in the operation flow described with FIG. 9, the drainage operation is performed after it is determined that the blood circuit 16 is a closed loop, the present invention is not limited to this embodiment. The blood purification apparatus 100 can also be configured to start the drainage operation, and then in a case where it is determined that the blood circuit 16 is a closed loop, continue the drainage operation, or in a case where the blood circuit 16 is not a closed loop, abort the drainage operation at that point.

In a case where the processing proceeds to S909, it means that some trouble is occurring for the reasons described earlier. Thus, in S909, the blood purification apparatus 100 aborts the operation for draining liquid in the blood circuit 16.

Third Embodiment

A third embodiment is a configuration having a third blood pump (BP3) installed between the blood purifier 19 and the V chamber 20 in the configuration of the first embodiment. The installation position of the BP3 may be the same as that in the second embodiment. Specifically, the V pressure increases as the BP3 rotates forwards, and the V pressure reduces as the BP3 rotates backwards. With reference to the flow in FIG. 2, changes made in the third embodiment are described below.

In S201, the blood purification apparatus 100 closes the ACLP, the VCLP, and the solenoid valve 22 and opens the PCLP to introduce air from the priming line, and rotates the BP1 forwards and the BP3 forwards. This operation causes the V side to be increased in pressure. The V side is brought to positive pressure relatively fast compared to the first embodiment because the BP1 and the BP3 are rotating forwards.

In S203, the blood purification apparatus 100 closes the PCLP and opens the ACLP and the solenoid valve 22, and then rotates the BP1 forwards and the BP3 backwards. Unlike the processing in S201, because the PCLP is closed, air is not introduced into the blood circuit 16, and the A side is brought to negative pressure. The blood purification apparatus 100 can reduce the pressure at the V side by rotating the BP3 backwards and opening the solenoid valve 22.

In this way, by using two blood pumps (the BP1 and the BP3), the third embodiment can perform self-evaluation more efficiently and faster than the first embodiment.

Mode of Present Invention

A first mode of the present invention is a blood purification apparatus including: a blood circuit having a blood removal side circuit into which blood removed from a patient flows and a blood return side circuit from which blood is returned to the patient and being able to form a closed circuit by having a first end portion of the blood removal side circuit and a first end portion of the blood return side circuit connected to each other via a blood purifier and by having a second end portion of the blood removal side circuit and a second end portion of the blood return side circuit connected to each other directly or indirectly; a blood pump provided at the blood circuit; a flow channel switch unit capable of switching between an open state in which fluid is able to flow through the first end portions of the blood removal side circuit and the blood return side circuit and a closed state in which the fluid is unable to flow through the first end portions of the blood removal side circuit and the blood return side circuit; a pressure detection unit that detects pressure inside the blood circuit; and a control unit that executes a drainage process of draining liquid remaining in the blood circuit to a predetermined drainage destination with the blood circuit forming the closed circuit. The control unit further executes a determination process in which the control unit generates a difference in pressure between the blood removal side circuit and the blood return side circuit by rotating the blood pump with the flow channel switch unit switched to the closed state, and then determines whether the blood circuit is the closed circuit by switching the flow channel switch unit to the open state and monitoring the difference in pressure based on a result of detection by the pressure detection unit, and in a case where it is determined in the determination process that the blood circuit is the closed circuit, the control unit executes the drainage process after the determination.

This offers an advantageous effect that in performing drainage of liquid in the AV-coupling-type blood circuit, the blood purification apparatus can self-evaluate that the blood circuit is in an AV coupled state.

In a second mode of the present invention according to the first mode, the blood pump is a first blood pump provided at the blood removal side circuit, the blood purification apparatus further comprises a second blood pump provided at the blood return side circuit. As the determination process, the control unit generates a difference in pressure between the blood removal side circuit and the blood return side circuit by switching the flow channel switch unit to the closed state and rotating the first blood pump and the second blood pump in a first direction and then determines whether the blood circuit is the closed circuit by switching the flow channel switch unit to the open state and monitoring the difference in pressure based on a result of detection by the pressure detection unit.

This offers an advantageous effect that in performing drainage of liquid in the AV-coupling-type blood circuit, the blood purification apparatus of a double-pump configuration can self-evaluate that the blood circuit is in an AV coupled state.

In a third mode of the present invention according to the first or second mode, the difference in pressure is a difference in pressure with the blood removal side circuit being negative pressure and the blood return side circuit being positive pressure.

This offers an advantageous effect that the blood purification apparatus can monitor the pressure difference between the blood removal side circuit at negative pressure and the blood return side circuit at positive pressure.

In a fourth mode of the present invention according to the first or second mode, in the determination process, the control unit determines whether the blood circuit is the closed circuit based on a result of the monitoring of the difference in pressure, and the result of the monitoring of the difference in pressure indicates that the difference in pressure generated between the blood removal side circuit and the blood return side circuit has reduced.

This offers an advantageous effect that the result of the monitoring performed by the blood purification apparatus indicates that the difference in pressure generated between the blood removal side circuit and the blood return side circuit has reduced.

In a fifth mode of the present invention according to the first mode, the blood purification apparatus further includes an introduction portion that introduces a first fluid into the blood circuit, the first fluid being for draining the liquid remaining in the blood circuit. With the flow channel switch unit being switched to the open state, the control unit introduces the first fluid from the introduction portion into the blood circuit and rotates the blood pump, thereby draining the liquid remaining in the blood circuit to the predetermined drainage destination.

This offers an advantageous effect that the blood purification apparatus can drain liquid remaining in the blood circuit to a predetermined drainage destination by introducing the first fluid into the blood circuit and rotating the blood pump.

In a sixth mode of the present invention according to the fifth mode, introduction material is air, physiological saline solution, or dialysate.

This offers an advantageous effect that the blood purification apparatus introduces air, physiological saline solution, or dialysate into the blood circuit in the drainage process.

A seventh mode of the present invention is a method executed by a blood purification apparatus including a blood circuit having a blood removal side circuit into which blood removed from a patient flows and a blood return side circuit from which blood is returned to the patient and being able to form a closed circuit by having a first end portion of the blood removal side circuit and a first end portion of the blood return side circuit connected to each other via a blood purifier and having a second end portion of the blood removal side circuit and a second end portion of the blood return side circuit connected to each other directly or indirectly; a blood pump provided at the blood circuit, a flow channel switch unit capable of switching between an open state in which fluid is able to flow through the first end portions of the blood removal side circuit and the blood return side circuit and a closed state in which the fluid is unable to flow through the first end portions of the blood removal side circuit and the blood return side circuit; a pressure detection unit that detects pressure inside the blood circuit, and a control unit that executes a drainage process of draining liquid remaining in the blood circuit to a predetermined drainage destination with the blood circuit forming the closed circuit. The method includes: generating, by the control unit, a difference in pressure between the blood removal side circuit and the blood return side circuit by rotating the blood pump with the flow channel switch unit switched to the closed state; determining, by the control unit, whether the blood circuit is the closed circuit by switching the flow channel switch unit to the open state and monitoring the difference in pressure based on a result of detection by the pressure detection unit; and in a case where it is determined in the determination process that the blood circuit is the closed circuit, executing, by the control unit, the drainage process after the determination.

This offers an advantageous effect that in performing drainage of liquid in the AV-coupling-type blood circuit, the blood purification apparatus can self-evaluate that the blood circuit is in an AV coupled state.

Although the principle of the present invention has been described above with reference to exemplary embodiments, those skilled in the art will understand that various embodiments modified in configurations and details can be implemented without departing from the gist of the present invention. Specifically, the present invention may be implemented as modes such as, for example, a system, an apparatus, a method, a program, or a storage medium.

REFERENCE SIGNS LIST

100 blood purification apparatus
11 patient connection portion of blood removal circuit
12 patient connection portion of blood return circuit
13 AV coupled state
14 A chamber
15 A pressure sensor
16 blood circuit
17 DI chamber
18 DI pressure sensor
19 blood purifier
20 V chamber
21 V pressure sensor
22 solenoid valve
23 drainer
24 controller
25 SN chamber
26 SN pressure sensor
30 first direction
40 second direction

The invention claimed is:

1. A blood purification apparatus comprising:

a blood circuit having a blood removal side circuit into which blood removed from a patient flows and a blood return side circuit from which blood is returned to the patient and being able to form a closed circuit by having a first end portion of the blood removal side circuit and a first end portion of the blood return side circuit connected to each other via a blood purifier and by having a second end portion of the blood removal side circuit and a second end portion of the blood return side circuit connected to each other directly or indirectly;

a blood pump provided at the blood circuit;

a flow channel switch unit capable of switching between an open state in which fluid is able to flow through the first end portions of the blood removal side circuit and the blood return side circuit and a closed state in which the fluid is unable to flow through the first end portions of the blood removal side circuit and the blood return side circuit, wherein the flow channel switch unit comprises clamps attached to the blood circuit;

a pressure detection unit that detects pressure inside the blood circuit; and a control unit that executes a drainage process of draining liquid remaining in the blood circuit to a predetermined drainage destination with the blood circuit forming the closed circuit, wherein the control unit further executes a determination process comprising:

generating, by the control unit, a difference in pressure between the blood removal side circuit and the blood return side circuit by rotating the blood pump with the flow channel switch unit switched to the closed state;

determining, by the control unit, whether the blood circuit is in the closed state by switching the flow channel switch unit to the open state and monitoring the difference in pressure based on a result of detection by the pressure detection unit; and in a case where it is determined that the blood circuit is in the closed state, executing, by the control unit, the drainage process.

2. The blood purification apparatus according to claim 1, wherein the blood pump is a first blood pump provided at the blood removal side circuit, the blood purification apparatus further comprises a second blood pump provided at the blood return side circuit, wherein in the determination process, the control unit generates a difference in pressure between the blood removal side circuit and the blood return side circuit by switching the flow channel switch unit to the closed state and rotating the first blood pump and the second blood pump in a first direction and then determines whether the blood circuit is in the closed state by switching the flow channel switch unit to the open state and monitoring the difference in pressure based on a result of detection by the pressure detection unit.

3. The blood purification apparatus according to claim 1, wherein the difference in pressure is a difference in pressure with the blood removal side circuit being negative pressure and the blood return side circuit being positive pressure.

4. The blood purification apparatus according to claim 1, wherein in the determination process, the control unit determines whether the blood circuit is in the closed state based on a result of the monitoring of the difference in pressure, and the result of the monitoring of the difference in pressure indicates that the difference in pressure generated between the blood removal side circuit and the blood return side circuit has reduced.

5. The blood purification apparatus according to claim 1, further comprising an introduction portion that introduces a first fluid into the blood circuit, the first fluid being for draining the liquid remaining in the blood circuit, wherein with the flow channel switch unit being switched to the open state, the control unit introduces the first fluid from the introduction portion into the blood circuit and rotates the blood pump, thereby draining the liquid remaining in the blood circuit to the predetermined drainage destination.

6. The blood purification apparatus according to claim 5, wherein the first fluid is air, physiological saline solution, or dialysate.

7. A method executed by a blood purification apparatus including a blood circuit having a blood removal side circuit into which blood removed from a patient flows and a blood return side circuit from which blood is returned to the patient and being able to form a closed circuit by having a first end portion of the blood removal side circuit and a first end portion of the blood return side circuit connected to each other via a blood purifier and having a second end portion of the blood removal side circuit and a second end portion of the blood return side circuit connected to each other directly or indirectly;

a blood pump provided at the blood circuit, a flow channel switch unit capable of switching between an open state in which fluid is able to flow through the first end portions of the blood removal side circuit and the blood return side circuit and a closed state in which the fluid is unable to flow through the first end portions of the blood removal side circuit and the blood return side circuit, wherein the flow channel switch unit comprises clamps attached to the blood circuit;

a pressure detection unit that detects pressure inside the blood circuit, and a control unit that executes a drainage process of draining liquid remaining in the blood circuit to a predetermined drainage destination with the blood circuit forming the closed circuit, the method comprising:

generating, by the control unit, a difference in pressure between the blood removal side circuit and the blood return side circuit by rotating the blood pump with the flow channel switch unit switched to the closed state;

determining, by the control unit, whether the blood circuit is in the closed state by switching the flow channel switch unit to the open state and monitoring the difference in pressure based on a result of detection by the pressure detection unit; and in a case where it is determined that the blood circuit is in the closed state, executing, by the control unit, the drainage process.

8. The blood purification apparatus according to claim 1, wherein the flow channel switch unit comprises a clamp attached to the blood removal side circuit and a clamp attached to the blood return side circuit.

9. The method according to claim 7, wherein the flow channel switch unit comprises a clamp attached to the blood removal side circuit and a clamp attached to the blood return side circuit.

* * * * *